US00PP34954P2

(12) United States Plant Patent van Laere et al.

(10) Patent No.: US PP34,954 P2
(45) Date of Patent: Jan. 31, 2023

(54) *VIBURNUM* PLANT NAMED 'ILVOMONO'

(50) Latin Name: *Viburnum plicatum*
Varietal Denomination: ILVOMONO

(71) Applicant: Spring Meadow Nursery Inc., Grand Haven, MI (US)

(72) Inventors: Katrijn van Laere, Melle (BE); Johan van Huylenbroeck, Melle (BE)

( * ) Notice: Subject to any disclaimer, the term of this patent is extended or adjusted under 35 U.S.C. 154(b) by 0 days.

(21) Appl. No.: 17/726,850

(22) Filed: Apr. 22, 2022

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

(56) References Cited

PUBLICATIONS

Community Plant Variety Office—CPVO Registe, Application Consultation, S2/S3 Pubication, citation for 'ILVOMONO'.*

* cited by examiner

*Primary Examiner* — Susan McCormick Ewoldt
(74) *Attorney, Agent, or Firm* — Cassandra Bright

(57) ABSTRACT

A new and distinct cultivar of *Viburnum* plant named 'ILVOMONO' is disclosed, characterized by a compact, spherical shape, pink flowers turning to white, and greyed-red autumn foliage. The new variety is a *Viburnum*, normally produced as an outdoor garden or container plant.

2 Drawing Sheets

Latin name of the genus and species: *Viburnum plicatum.*
Variety denomination: 'ILVOMONO'.

BACKGROUND OF THE INVENTION

The new *Viburnum* cultivar is a product of a planned breeding program conducted by the inventor in Melle, Belgium. The open-pollination resulting in this new variety was made during spring of 2009. The objective of the breeding program was to develop new cultivars of *Viburnum* for commercial horticultural purposes.

The seed parent of 'ILVOMONO' is the unpatented *Viburnum plicatum* 'Watanabei'. The pollen parent is unidentified. The new variety was identified as a potentially interesting selection in 2012, at a research greenhouse in Melle, Belgium.

The first asexual propagation of 'ILVOMONO' was carried out in 2019 by rooting stem cuttings at the same research greenhouse Melle, Belgium, and has been asexually reproduced repeatedly. 'ILVOMONO' has been found to retain its distinctive characteristics through successive asexual propagations.

SUMMARY OF THE INVENTION

The cultivar 'ILVOMONO' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ILVOMONO' These characteristics in combination distinguish 'ILVOMONO' as a new and distinct *Viburnum* cultivar:

1. Abundant pink flowers in the beginning of flowering period, turning to white.

2. Flowering from May to July, with a second flowering period possible in September.
3. Compact, spherical plant shape.
4. Very dense plant with dense branching.
5. Small leaves with a greyed-red autumn coloration.

PARENT COMPARISON

Plants of the new cultivar 'ILVOMONO' are similar to plants of the seed parent in most horticultural characteristics, however, plants of 'ILVOMONO' differ in the following:

1. Flowers of the new variety begin pinkish and turn white; flowers of the seed parent variety are consistently white.
2. Plants of the new variety are more compact and dense than plants of the seed parent.

The pollen parent is unidentified.

COMMERCIAL COMPARISON

Plants of the new cultivar 'ILVOMONO' can be compared to the commercial variety *Viburnum* 'ILVOAWAI', U.S. Plant patent application Ser. No. 17/726,805. These varieties are similar in most horticultural characteristics; however, 'ILVOMONO' differs in the following:

1. Plants of 'ILVOMONO have a nearly equal height and width compared to plants of 'ILVOAWAI' which are wider than tall.
2. Flowers of 'ILVOAWAI' are a different shade of pink during the pink phase of flowering than the pink flowers of 'ILVOMONO'. Flowers of 'ILVOMONO' are colored near Red-Purple 63D at maturing, changing to White 155D. Flowers of 'ILVOAWAI' are colored Red-Purple 65A, 65D over White 155A and do not turn completely white.

BRIEF DESCRIPTION OF THE PHOTOGRAPHS

This new *Viburnum* is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new *Viburnum* cultivar. Plants are approximately 3 years, planted in the ground.

DETAILED BOTANICAL DESCRIPTION

Figure 1:
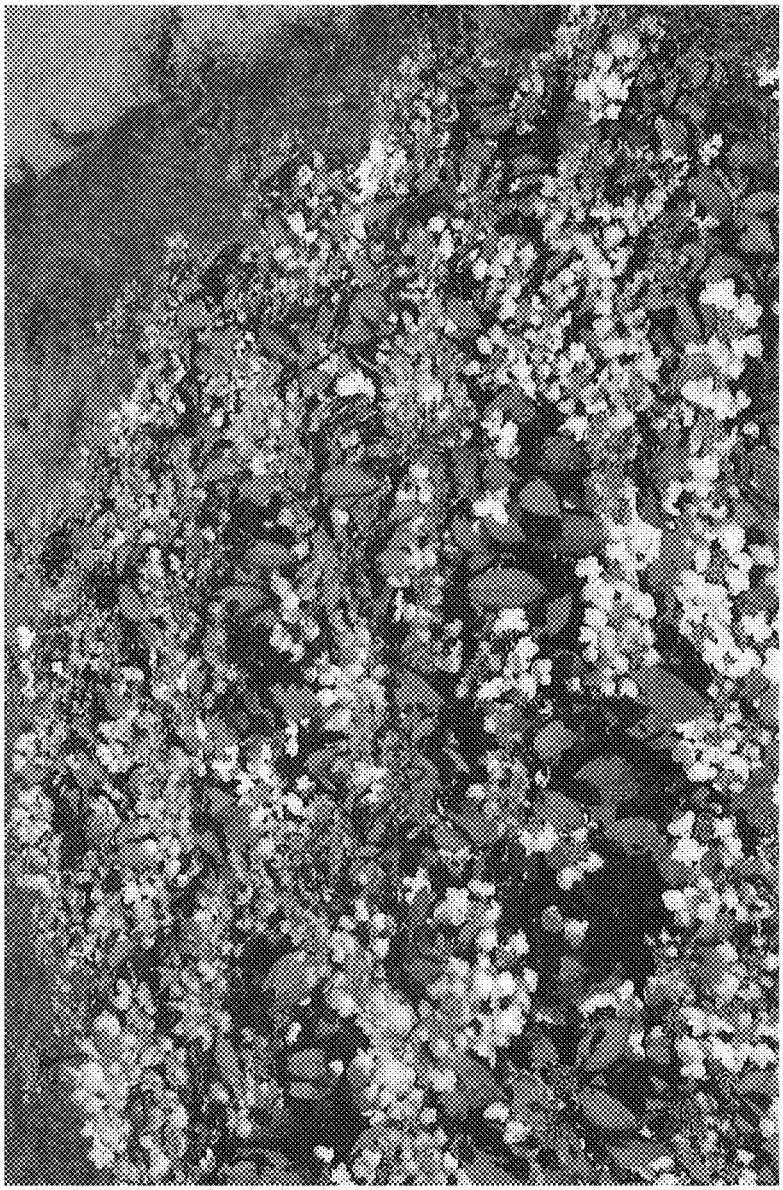
FIG. 1 is a color photograph of a field-grown plant of 'ILVOMONOI' in Grand Haven, Mich.
Figure 2:
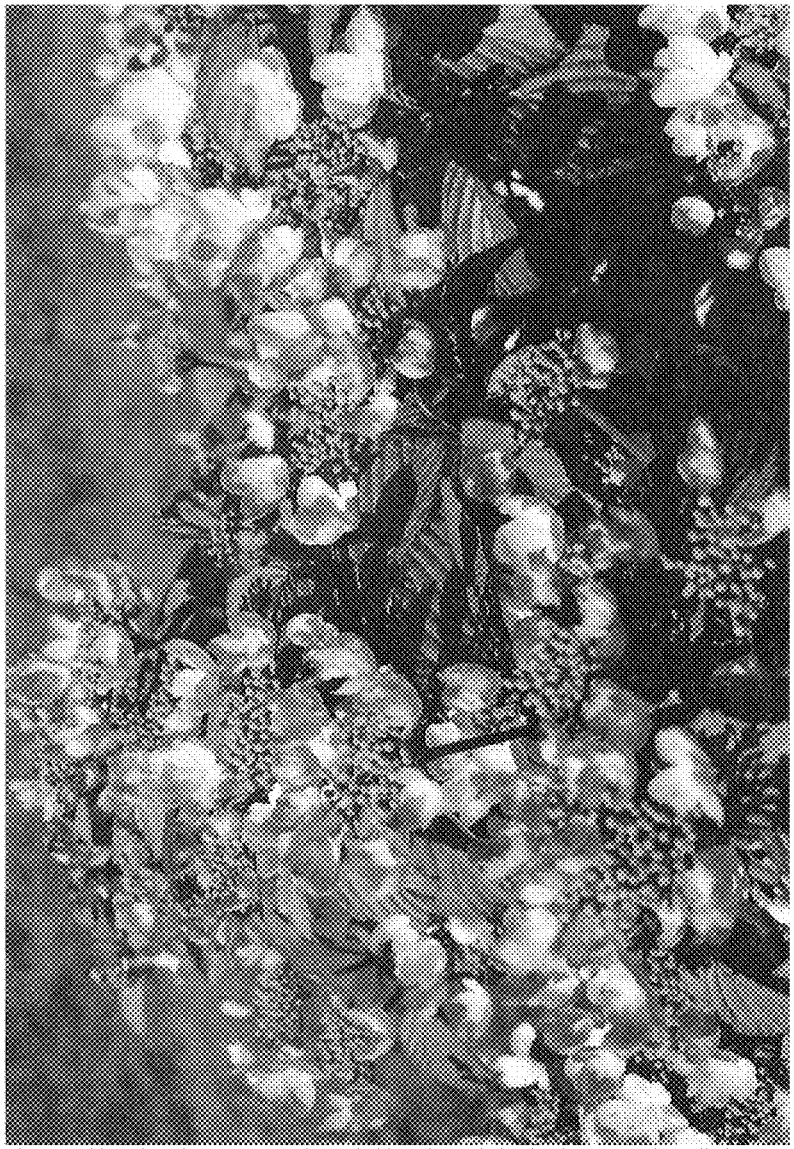
FIG. 2 is a color photograph showing inflorescences of 'ILVOMONO' grown in Grand Haven, Mich.

The following is a detailed description of the botanical characteristics of the new and distinct *Viburnum* variety plant known by the denomination 'ILVOMONO'. The detailed description was taken on a seven-year-old field-grown plant in Melle, Belgium in 2021. All colors cited herein refer to The Royal Horticultural Society Colour Chart (The Royal Horticultural Society (RHS), London, Sixth Edition). Where specific dimensions, sizes, colors, and other characteristics are given, it is to be understood that such characteristics are approximations or averages set forth as accurately as practicable.

Botanical classification: *Viburnum plicatum* 'ILVOMONO'.

PROPAGATION

Typical method: Softwood cuttings.
Time to initiate rooting: 28 days at approximately 27° C.
Time to produce a rooted young plant: About 3 months at approximately 27° C.
Root description: Dense, free branching roots of moderate thickness. Colored yellow-white, not accurately measured with an RHS chart.

PLANT

Plant type: Perennial flowering shrub.
Plant description:
- *Growth habit.*—Upwards and outwards.
- *Shape.*—Compact, spherical.
- *Height.*—120 cm.
- *Width.*—120 cm.
- *Growth rate.*—Good.
- *Vigor.*—Moderately vigorous.
- *Branching habit.*—Basal, freely branching.
- *Pinching required?.*—Not required, but if pinched, second flowering possible.

Stem:
- *Lateral branch length.*—Up to 70 cm.
- *Lateral branch diameter.*—0.5 to 0.8 cm.
- *Internode length.*—4 to 6 cm.
- *Stem texture.*—Smooth, glabrous.
- *Color.*—RHS Grey-Brown 199B.
- *Strength.*—Strong, erect stems.
- *Pubescence.*—None.

FOLIAGE

Leaf:
- *Persistence.*—Deciduous to semi-evergreen in warmer climates.
- *Arrangement.*—Opposite, single.
- *Shape.*—Elliptic.
- *Width.*—3 cm.
- *Length.*—6 cm.
- *Apex.*—Acuminate.
- *Base.*—Acute.
- *Venation.*—Reticulate.
- *Vein color.*—Near RHS Green 137A.
- *Margins.*—Dentate.
- *Pubescence.*—Upper side.
- *Texture, upper side.*—Felty, with little hairs.
- *Texture, under side.*—Felty, with little hairs.
- *Color.*—Immature upper surface: RHS Green 143A. Immature lower surface: RHS Green 143B. Mature upper surface: RHS Green 143A to 141A; autumn coloration to Greyed-Red 178C and 178D. Mature lower surface: RHS Green 143A to 141B; autumn coloration to Greyed-Red 178C and 178D.

Petiole:
- *Length.*—About 1 cm.
- *Diameter.*—About 0.1 cm.
- *Color, upper side.*—RHS Red-Purple 60A and 60B and 59B.
- *Color, under side.*—RHS Red-Purple 60A and 60B and 59B.
- *Texture, upper side.*—Very little hairs.
- *Texture, under side.*—Very little hairs.

FLOWER

Description: Inflorescences on terminal ends of branches.
Inflorescence type: Compound umbel, lacecap.
Inflorescence diameter: Average 5 cm.
Flowering season: May through July.
Longevity on plant: 3 months.
Persistent or self-cleaning: Persistent.
Fragrance: None.
Flower:
- *Shape.*—Fertile and Sterile flowers: Rotate, wheel-shaped.
- *Aspect.*—Fertile and Sterile flowers: Upright, outward.

Bud:
- *Color, fertile flowers.*—Just before opening: RHS Yellow-White 158B and 158C, with a blush of Red-Purple 60A.
- *Size sterile flower buds.*—1 mm in diameter and length.

Petals:
- *Number.*—4 to 5.
- *Appearance.*—Sterile flowers: 4 petals in a single whorl, sometimes a $5^{th}$ small petal. Fertile flowers: 5 petals in a single whorl.
- *Arrangement.*—Rotated (both fertile and sterile flowers), arranged in a single whorl.
- *Fused.*—Sterile flowers: Yes, fused at base. Fertile flowers: No.
- *Sterile flower petal length.*—Average 1 cm.
- *Sterile flower petal width.*—Average 5 mm.
- *Fertile flower petal length.*—Average 1.5 mm.
- *Fertile flower petal width.*—Average 1 mm.
- *Shape.*—Obovate-rounded.
- *Margin.*—Entire.
- *Apex.*—Obtuse.
- *Base.*—Rounded.
- *Texture.*—Smooth, both sides.
- *Color.*—Sterile flowers upper and lower surfaces: RHS Yellow-White 158A-B. Fertile flowers upper and lower surfaces: Opening color near RHS Red-Purple 63A, maturing to 63D, changing to White 155A after 6 to 8 weeks of full maturity (pink color stays for at least one month).

Sepals: About 0.5 mm in size. Too minute for accurate measurement.
Calyx: Very small, wheel-shaped.

Peduncles:
*Length.*—Average 1.5 cm.
*Diameter.*—Average 1 mm.
*Color.*—Near RHS Yellow-Green 144B.
*Texture.*—Smooth.
*Strength.*—Strong.

Pedicels:
*Length.*—Average 3 mm.
*Diameter.*—Average 1 mm.
*Color.*—Near RHS Yellow-Green 144B.
*Texture.*—Smooth, glabrous.
*Strength.*—Moderately strong.

REPRODUCTIVE ORGANS

Gynoecium:
*Pistil number.*—1.
*Stigma color.*—RHS White 155A.

Androecium:
*Stamen number.*—5.
*Filament length.*—About 0.5 cm.
*Filament color.*—RHS White 155A.
*Anther shape.*—Rounded, 2-lobed.
*Anther size.*—About 0.5 mm.
*Anther color.*—RHS Yellow 4B-C.
*Amount of pollen.*—Plentiful.
*Pollen color.*—RHS Yellow 4B-C.

OTHER CHARACTERISTICS

Fruit:
*Quantity.*—1 per flower.
*Length.*—About 4 mm.
*Diameter.*—About 3 mm.
*Shape.*—Elliptic.
*Color.*—Near RHS Greyed-Red 178A and 178B, turning near Black 203A when dessicated.
*Texture.*—Smooth.
*Seed.*—One round seed produced per fruit, developing in the Fall.

Disease and insect resistance: No disease detected in 7 years.
Temperature tolerance: Tolerant from 40° C. to −10° C.

What is claimed is:

1. A new and distinct cultivar of *Viburnum* plant named 'ILVOMONO' as herein illustrated and described.

* * * * *